US008077828B2

(12) United States Patent
Aoyama (10) Patent No.: US 8,077,828 B2
(45) Date of Patent: Dec. 13, 2011

(54) RADIATION IMAGING DEVICE AND RADIATION IMAGING METHOD

(75) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 12/396,495

(22) Filed: Mar. 3, 2009

(65) Prior Publication Data

US 2009/0225940 A1 Sep. 10, 2009

(30) Foreign Application Priority Data

Mar. 6, 2008 (JP) ................. 2008-056445

(51) Int. Cl.
G01N 23/087 (2006.01)
H05G 1/32 (2006.01)
H05G 1/42 (2006.01)

(52) U.S. Cl. ............ 378/62; 378/91; 378/108; 378/112; 378/113; 378/114

(58) Field of Classification Search .......... 378/8, 5, 378/16, 19, 42, 62, 91, 95, 96, 98.8, 98.9, 378/98.11, 108, 112, 113, 114, 115, 116
See application file for complete search history.

(56) References Cited

U.S. PATENT DOCUMENTS

| | | | | |
|---|---|---|---|---|
| 4,160,906 A | * | 7/1979 | Daniels et al. .................. 378/97 |
| 4,403,337 A | * | 9/1983 | Kleinman ........................ 378/95 |
| 5,231,651 A | * | 7/1993 | Ozaki et al. ....................... 378/4 |
| 6,501,827 B1 | * | 12/2002 | Takasawa ..................... 378/116 |
| 6,714,623 B2 | * | 3/2004 | Sako et al. ................... 378/98.8 |
| 6,891,918 B2 | * | 5/2005 | Drummond et al. ............. 378/5 |
| 6,920,201 B2 | * | 7/2005 | Maack et al. ................. 378/116 |
| 6,944,269 B2 | * | 9/2005 | Schmitt .......................... 378/115 |
| 6,993,114 B2 | * | 1/2006 | Takasawa ................... 378/98.5 |
| 7,054,406 B2 | * | 5/2006 | Ikeda et al. ....................... 378/8 |
| 7,120,229 B2 | * | 10/2006 | Takasawa ................... 378/98.2 |
| 7,130,377 B2 | * | 10/2006 | Matsuno ........................ 378/96 |
| 7,428,294 B2 | * | 9/2008 | Spahn ............................ 378/62 |
| 7,502,445 B2 | * | 3/2009 | Shi et al. ....................... 378/115 |

FOREIGN PATENT DOCUMENTS

| | | |
|---|---|---|
| JP | 2002-243860 | 8/2002 |
| JP | 2002-325756 | 11/2002 |
| JP | 2003-284710 | 10/2003 |
| JP | 2004-261489 | 9/2004 |

* cited by examiner

*Primary Examiner* — Allen C. Ho (74) *Attorney, Agent, or Firm* — SOLARIS Intellectual Property Group, PLLC (57) ABSTRACT

When the same subject is to be imaged consecutively plural times, a radiation imaging device is controlled so as to change an imaging time interval between respective imagings according to a set imaging region of the subject. When a chest portion of a subject is to be imaged, a control section designates an image obtained at a second imaging as an image for diagnosis, image quality correction processing is not performed at a first imaging, and an imaging time interval is greatly reduced compared to when other regions are imaged, thereby reducing motion artifacts of an energy subtraction image. When regions other than a chest region are imaged, the control section designates an image obtained at a first imaging as an image for diagnosis, performs image quality correction processing at the first imaging, and an imaging time interval is increased compared to when the chest region is imaged.

16 Claims, 5 Drawing Sheets

FIG. 4

RADIATION IMAGING DEVICE AND RADIATION IMAGING METHOD

CROSS-REFERENCE TO RELATED APPLICATION

This application claims priority under 35 USC 119 from Japanese Patent Application No. 2008-056445, the disclosure of which is incorporated by reference herein.

BACKGROUND OF THE INVENTION

1. Field of the Invention

The present invention relates to a radiation imaging device and a radiation imaging method, and in particular, to a radiation imaging device and a radiation imaging method that each detect, as an image, radiation rays that have passed through a subject, and image the same subject consecutively plural times.

2. Description of the Related Art

In the imaging of radiation images, a technique is known in which the same region of an imaging subject is imaged at different tube voltages, and the images obtained at the imaging of each tube voltage are weighted, and a differential is calculated, thereby emphasizing in the image one of image portions corresponding to hard structures such as bones or the like, or image portions corresponding to soft structures, and removing the other, thereby obtaining an energy subtraction image.

As a method of creating energy subtraction images, a conventional technique is known in which a photo-stimulable luminescent body is used with an X-ray detector, and a filter such as a copper plate or the like is placed between two detectors, such that two images with different tube voltages are substantially obtained from a single imaging, and an energy subtraction image is created from these images.

Further, an X-ray system that uses a semiconductor detector has come to be used, and it has become possible to take consecutive X-ray images in a short period of time and create energy subtraction images from two images taken consecutively. However, due to a photoconductive effect at a semiconductor detector, image information of the image taken at a first imaging remains at the detector (hereafter sometimes referred to as an "afterimage"), and this affects the image taken at the second imaging. Japanese Patent Application Laid-Open (JP-A) No. 2002-243860 discloses a technique in which, when two consecutive images are taken, the first imaging is performed at a low dose of radiation, and the second imaging is performed at a high dose of radiation, and a period of time between each imaging is reduced, taking into consideration for the photoconductive effect.

JP-A No. 2004-261489 discloses a technique in which, when two consecutive images are taken, the first imaging is performed at a low dose of radiation and image information is read in a high-speed, low-definition mode, and the second imaging is performed at a high dose of radiation, and image information is read in a low-speed, high-definition mode, thereby reducing the period of time between imagings and reducing the effect of movement of the subject's body (motion artifacts).

Further, JP-A No. 2003-284710 discloses performing a first imaging at a low dose of radiation, and obtaining a first image data aggregate, and after reducing gain and increasing image acquiring resolution, performing a second imaging at a high dose of radiation and obtaining a second image data aggregate, and obtaining a first and a second offset image.

Moreover, as a technique related to the above, JP-A No. 2002-325756 discloses observing the cardiac cycle of a patient and finding a first cardiac trigger, and imaging the patient with a first X-ray energy according to the first cardiac trigger and forming a first X-ray image, observing the cardiac cycle of a patient and finding a second cardiac trigger, and imaging the patient with a second X-ray energy according to the second cardiac trigger, and forming a second X-ray image.

The above-mentioned techniques each reduce motion artifacts in an energy subtraction image. In particular, the above-disclosed techniques aim to reduce motion artifacts by reducing an imaging time interval between plural imagings as much as possible. In this regard, images obtained by plural imagings to create an energy subtraction image are desired to use not only for the creation of an energy subtraction image, but also for diagnosis and the like. However, although a high quality image is desired for diagnosis, a decrease in an imaging time interval is linked to a decrease in image quality, for example, as in the high-speed, low-definition mode of the above-mentioned JP-A No. 2004-261489, and thus reducing an imaging time interval and increasing image quality have been conflicting goals.

SUMMARY OF THE INVENTION

The present invention considers the above issues, and aims to address them by providing a radiation imaging device that takes plural consecutive images of the same subject, and reduces motion artifacts, thereby obtaining a high quality image that can be used for diagnosis.

A first aspect of the present invention provides a radiation imaging device, including: a radiation ray generation unit that generates radiation rays; an image detection unit that detects as an image radiation rays that are emitted by the radiation ray generation unit and pass through a subject; and a control unit that, when the same subject is to be imaged consecutively plural times, changes an imaging time interval between imagings according to a set imaging region of the subject.

When the same subject is to be imaged consecutively plural times, it is desirable to make an imaging time interval as small as possible in order to reduce motion artifacts. However, when imaging a chest portion or the like, in which organs such as the heart, which move due to an involuntary muscle, enter into the imaging range, motion artifacts are a significant problem. In contrast, when the imaging range includes parts that are moved by voluntary muscles, even if an imaging time interval is somewhat long, motion artifacts can be suppressed by other methods (such as holding the imaging portion from the outside, requesting the subject not to move the imaging region, etc.). Thus, the effect that an imaging time interval has on the creation of motion artifacts differs according to the imaging region of the subject. If a large dose of radiation rays are used in imaging, an afterimage becomes pronounced, and if an imaging time interval is small, then a subsequent image is affected thereby. For this reason, it is necessary to lengthen the imaging time interval as the dose of radiation rays increases; however, the most appropriate dose of radiation when imaging depends on the imaging region of the subject. Further, when an energy subtraction image is to be obtained by taking plural images having varying radiation ray dosages, the most appropriate image for use in diagnosis, of an image taken with a low tube voltage and an image taken with a high tube voltage, depends on the region of the subject which is imaged. Moreover, when plural images are taken with differing tube voltages, since it is difficult to control a radiation ray generation unit so as to lower the tube voltage in a short period of time, it is desirable to perform imaging with a low tube voltage followed by imaging with a high tube voltage.

Since an imaging time interval is related to image quality and the reduction of motion artifacts, each of the effect that an imaging time interval has on the creation of motion artifacts, an appropriate radiation ray dose and a tube voltage to be used when imaging to obtain an image which can be used for diagnosis, and the like, differ according to the region of the subject to be imaged. Thus, in the first aspect of the present invention, when the same subject is to be imaged consecutively plural times, an imaging time interval between imagings can be changed according to a set imaging region of a subject.

Therefore, for example, when imaging an imaging region in which the creation of motion artifacts is greatly influenced by an imaging time interval, motion artifacts can be reduced by reducing the imaging time interval, and when imaging to obtain an image which can be used for diagnosis in which a comparatively large dose of radiation rays is used, an imaging time interval can be increased to obtain a high quality image. According to the radiation imaging device of the first aspect of the present invention, when the same subject is to be imaged consecutively plural times, motion artifacts can be reduced and a high quality image which can be used for diagnosis can be obtained.

The radiation imaging device of the first aspect of the present invention is preferably configured such that, when the same subject is to be imaged consecutively plural times, a control unit controls the radiation ray generation unit so that the radiation ray dose at each imaging increases monotonically, regardless of the set imaging region of the subject. As described above, to reduce the effect of an afterimage, it is necessary to increase an imaging time interval as the dose of radiation rays increases when imaging. A radiation imaging device with the above configuration controls a radiation ray generation unit during each imaging such that a radiation ray dose increases monotonically, such that in n imagings, an imaging that uses a maximum radiation ray dose is performed at the nth imaging, and by reducing an average imaging time interval over n−1 imagings, motion artifacts can be reduced.

In the radiation imaging device of the first aspect of the present invention, since it is difficult to control to reduce a high tube voltage to a low tube voltage in a short space of time, it is preferable to adopt a configuration in which, when the same subject is to be imaged consecutively plural times, a control unit controls the radiation ray generation unit so that the radiation ray tube voltage at each imaging increases monotonically, regardless of the set imaging region of the subject. Thereby, motion artifacts can be reduced by reducing the average imaging time interval over n−1 imagings.

In the above radiation imaging device, it is also preferable that the control unit switches between outputting an image obtained at a first imaging as an image for diagnosis or outputting an image obtained at a second imaging as an image for diagnosis, according to the set imaging region of the subject.

From amongst plural images obtained by plural imagings, an image obtained at a high tube voltage is appropriate for a chest portion or the like, and an image obtained at a low tube voltage is appropriate for a lumbar spine, the limbs or the like. According to the above radiation imaging device, an image appropriate for diagnosis can be obtained for each imaging region.

The radiation imaging device of the first aspect of the present invention may be implemented with a configuration in which an imaging time interval is changed according to a set imaging region of a subject, for example, by providing a storage section that stores set values of an imaging time interval between plural imagings with respect to each imaging region of a subject; and a control unit reads the set value of the imaging time interval from the storage section according to the set imaging region of the subject, and uses the value for control of the imaging time interval.

In the radiation imaging device configured as above, it is preferable that a control unit, when instructed to change an imaging time interval via an instruction section, changes a value of the imaging time interval read from the storage section in accordance with the instruction, and uses the changed value for control of the imaging time interval. Thereby, it is possible to further adjust an imaging time interval to reduce motion artifacts, by, for example, measuring a cardiac cycle of an imaging subject and changing an imaging time interval such that it approaches the measured cardiac cycle, or the like.

In the above radiation imaging device, a configuration may be adopted in which parameters that determine imaging conditions for each imaging of plural imagings are stored with respect to each imaging region in the storage section, and a control unit reads the parameters corresponding to the set imaging region of a subject from the storage section, and uses the parameters for control of imaging conditions for each imaging of plural imagings. The above imaging conditions may include at least one of the tube voltage of the radiation ray generation unit, a tube current, a radiation ray generation time, or a distance from the subject.

In the above radiation imaging device, it is preferable that a control unit, when imaging conditions for a particular instance of imaging of plural imagings are changed via the instruction section, changes the imaging conditions for the particular instance of imaging of plural imagings set by parameters read from the storage section, and changes imaging conditions for a different instance of imaging of the plural imagings based on the changed imaging conditions of the particular instance of imaging. When taking a radiation image, it may be necessary to change imaging conditions according to a bodily frame or the like of an imaging subject. In the above radiation imaging device, since imaging conditions for a particular instance of imaging of plural imagings are changed via the instruction section, and imaging conditions for instances other than the particular instance are changed in accordance therewith, changing imaging conditions for each imaging of plural imagings can be easily performed.

Further, considering that, upon creating an energy subtraction image, a large difference in tube voltage between plural images used to created the energy subtraction image can obtain a high contrast energy subtraction image of an appropriate image quality, it is preferable that the above radiation imaging device is configured such that, when the imaging conditions include a tube voltage of the radiation ray generation, and when the tube voltage is changed in a particular instance of imaging, a control unit changes the tube voltage for an instance of imaging different from the particular instance of imaging, such that the difference in tube voltages between plural imagings is not less than a difference in tube voltage set by a parameter read from the storage section.

According to the above, even when the tube voltage of a particular instance of multiple instances of imaging is instructed to be changed, since the tube voltage of an instance of imaging other than the particular instance is changed in accordance therewith, it is possible to prevent a reduction in image quality of an energy subtraction image when the tube voltage of a particular instance of imaging is instructed to be changed.

Further, it is preferable that in the radiation imaging device of the first aspect of the present invention, a correction unit is provided that, between respective imagings, while acquiring from an image detection unit an image detected by an image detection unit, performs image quality correction processing to improve image quality of the acquired image, and a control unit switches between the correction unit performing or not performing image quality correction processing according to a set imaging region of the subject. When the above correction unit performs image quality correction processing, the image quality of an acquired image is increased, but since it takes time to acquire an image from the image detection unit, an imaging time interval until the next imaging is lengthened, causing a decrease in image quality of an energy subtraction image due to motion artifacts, depending on the imaging region of the subject.

Thus, the above radiation imaging device can switch between the correction unit performing or not performing image quality correction processing according to the set imaging region of the subject, and image quality correction processing can be performed or not performed as appropriate according to the imaging region of the subject. For example, if the imaging region is one where an imaging time interval has a large effect on the creation of motion artifacts, when taking an image not to be used for diagnosis, image quality correction processing is not performed by the correction unit, and the imaging time interval is reduced, thereby reducing motion artifacts. Similarly, if the imaging region is one in which a comparatively large dose of radiation rays is used when taking an image which can be used for diagnosis, the imaging time interval can be lengthened and image quality correction processing is performed by the correction unit, at least when taking the image to be used for diagnosis or the like, and thereby a high quality image can be obtained.

When the radiation imaging device of the first aspect of the present invention is provided with a correction unit that, between respective imagings, while acquiring from the image detection unit an image detected by the image detection unit, performs image quality correction processing to improve image quality of the acquired image, it is preferable that the control unit switches between the correction unit performing and not performing image quality correction processing in units of plural imagings. Thereby, it is possible to set and switch between whether the correction unit performs or does not perform image quality correction processing with respect to each image taken, and it is possible to perform frame by frame animation (semi-animation) imaging, in which imaging that focuses on an imaging time interval, or imaging that focuses on image quality, can be performed.

If the above radiation imaging device is configured such that the image detection unit is provided with plural pixel portions each provided with a switching portion that switches ON and OFF according to an ON or OFF signal supplied via a first signal line, and a retaining portion that retains a signal charge corresponding to an irradiated radiation ray dose, the correction unit, as image quality correction processing, may respectively acquire a signal output from a second signal line at each of when the switching portion is ON or OFF, and perform at least one of a leak correction processing, in which an OFF output signal is subtracted from an ON input signal, or an electronic noise suppression processing, in which an output signal is converted to digital data plural times and averaged.

The second aspect of the present invention provides a radiation imaging method, including: generating radiation rays consecutively plural times with respect to a single subject; performing plural imagings by detecting as images radiation rays that pass through the subject; and controlling to change an imaging time interval between the respective plural imagings according to a set imaging region of the subject.

As described above, since, in the present invention, when a single subject is to be imaged consecutively plural times, since an imaging time interval between plural imagings can be changed according to a set imaging region of the subject, thereby reducing motion artifacts, the present invention has the excellent effect of reducing motion artifacts and obtaining a high quality image which can be used for diagnosis or the like.

DETAILED DESCRIPTION OF THE INVENTION

Figure 1:
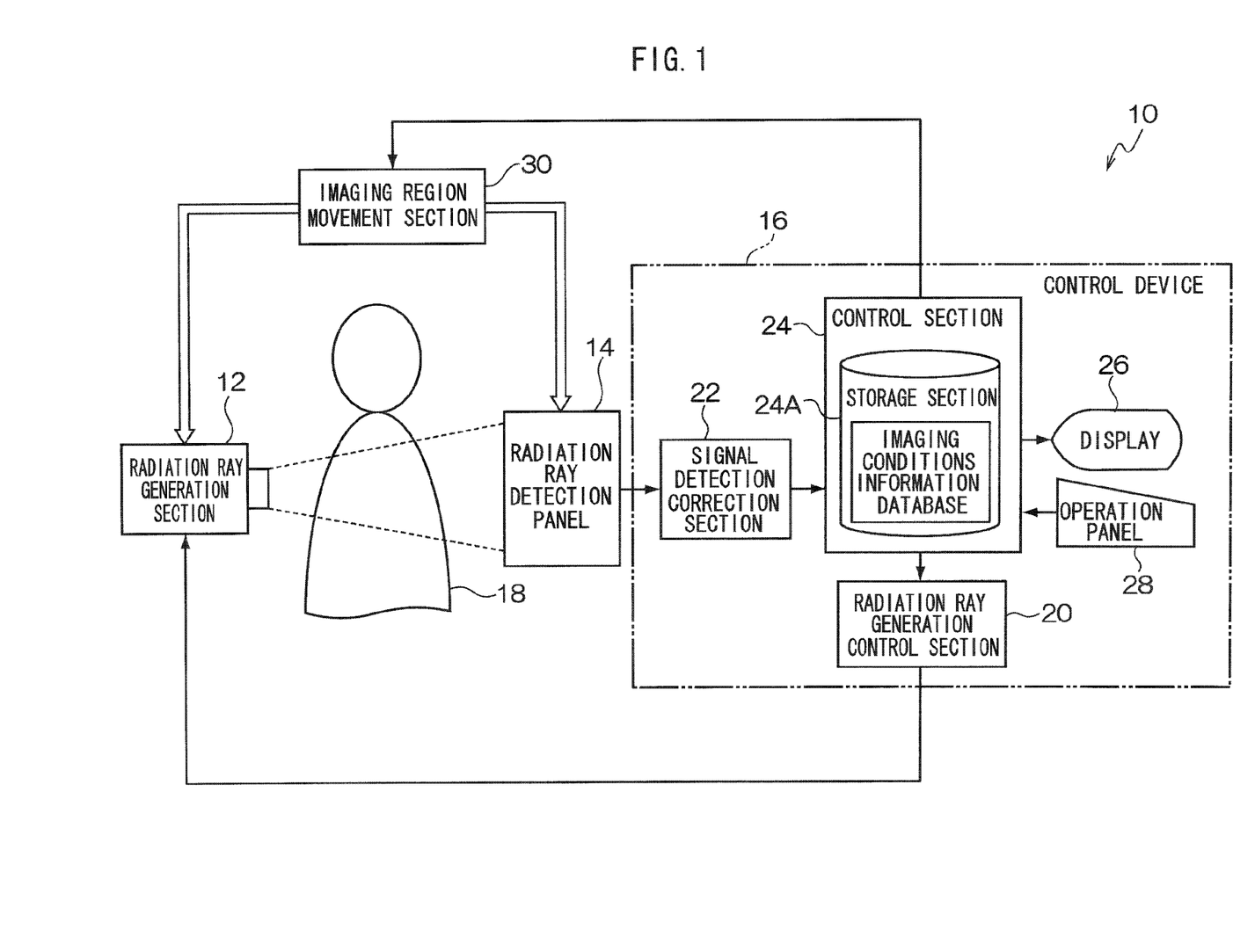
FIG. 1 is a block drawing showing a schematic configuration of the radiation imaging system according to the present embodiment.

An exemplary embodiment of the present invention is explained below in detail with reference to the drawings. FIG. 1 shows a radiation imaging system 10 according to the present embodiment. Radiation imaging system 10 includes a radiation ray generation section 12 that generates radiation rays (such as X rays or the like), a radiation ray detection panel 14 arranged spaced apart from radiation ray generation section 12, and a control device 16 including a microcomputer and various electrical circuits, which obtains image information from radiation ray detection panel 14 and performs various types of processing. Between radiation ray generation section 12 and radiation ray detection panel 14 is an imaging position at which a subject 18 is positioned during imaging. Radiation rays emitted from radiation ray generation section 12 pass through subject 18 positioned at the imaging position, and radiation rays carrying image information are incident on radiation ray detection panel 14.

Radiation imaging system 10 according to the present embodiment corresponds to the radiation imaging device of the present invention; radiation ray generation section 12 corresponds to the radiation ray generation unit of the present invention; radiation ray detection panel 14 corresponds to the image detection unit of the present invention; and control section 24 (described below) of control device 16 corresponds to the control unit of the present invention.

Control device 16 is provided with a radiation ray generation control section 20, a signal detection correction section 22, a control section 24, a display 26 which can display images and the like, and an operation panel 28 including an input device such as a keyboard or the like and a pointing device such as a mouse or the like. Radiation ray generation control section 20 is connected to radiation ray generation section 12 and control section 24, and according to instructions from control section 24, controls a radiation dose and the like of radiation rays generated by radiation ray generation section 12, by controlling, during radiation ray generation by radiation ray generation section 12, a tube voltage, a tube current, and a time of radiation ray generation. Further, each time subject 18 is imaged, signal detection correction section 22, which is explained in detail below, reads image signals from radiation ray detection panel 14, and performs conversion thereof to a digital image, and performs image quality correction processing (described in detail below) on the image data obtained by the conversion, such as leak correction processing, electrical noise suppression processing, and the like.

Control section 24 includes a microcomputer and the like, and, according to instructions input via operation panel 28, controls imaging of subject 18, performs image processing, such as creating an energy subtraction image, using image data input from signal detection correction section 22, and performs processing to provide a predetermined user interface via display 26 and operation panel 28. Control section 24 also includes a storage section 24A including an HDD (Hard Disk Drive) or nonvolatile memory such as flash memory, which stores an imaging conditions database, the content of which is explained below. Further, storage section 24A also stores a program that performs consecutive imaging processing, also described below.

Radiation imaging system 10 also includes an imaging region movement section 30, which includes an actuator or the like that enables radiation ray generation section 12 and radiation ray detection panel 14 to move, and which, when notified by control device 16 of a region of subject 18 to be imaged (for example, a chest, a lumbar spine, a limb, a breast, or the like), moves radiation ray generation section 12 and radiation ray detection panel 14 to a position for imaging the imaging region of subject 18 of which it has been notified. Since appropriate positions of radiation ray generation section 12 and radiation ray detection panel 14 for imaging the portion of subject 18 may change according to the bodily frame and the like of subject 18, if imaging region movement section 30 is instructed via operation panel 28 to adjust an imaging position, it may adjust the respective positions of radiation ray generation section 12 and radiation ray detection panel 14 according to the instructions.

Next, the configuration of radiation ray detection panel 14 and signal detection correction section 22 will be described. In radiation ray detection panel 14, a photoelectric conversion layer (not shown) that absorbs radiation rays and converts them to electric charges is formed above a TFT active matrix substrate 34 shown in FIG. 2, and a bias electrode (not shown) connected to a voltage source is formed above the photoelectric conversion layer. The photoelectric conversion layer is, for example, made of non-crystalline amorphous selenium (a-Se) including mainly selenium (e.g. selenium content is 50% or more), and when radiation rays are incident thereon, charges (electron/hole pairs) having a charge quantity corresponding to the radiation dose are generated therein, and thereby the incident radiation rays are converted to charges. Thus, image information carried by incident radiation rays is converted to charge information.

Figure 2:
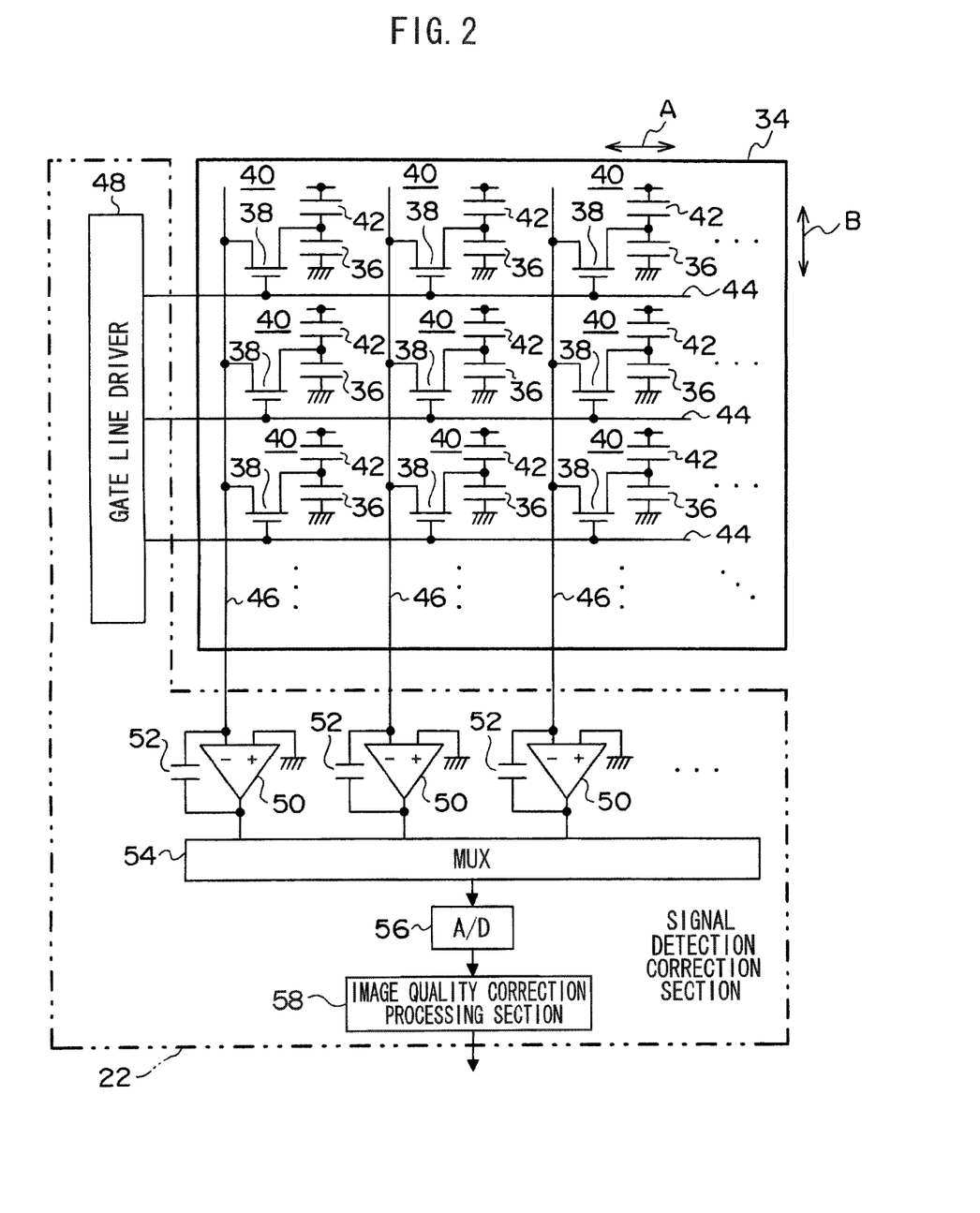
FIG. 2 is a schematic configuration drawing of a radiation ray detection panel and a signal detection correction section.

Above TFT active matrix substrate 34 are storage capacitors 36 that store charges generated at the photoelectric conversion layer, and pixel portions 40 including TFTs 38 that read charges stored in storage capacitors 36 arranged in a matrix (in FIG. 2, bias electrodes and a photoelectric conversion layer corresponding to individual pixel portions 40 are represented schematically by photoelectric conversion portion 42). As shown in FIG. 2, plural gate lines 44, that turn TFTs 38 of pixel portions 400N and OFF, are arranged in the direction of arrow A, and plural data lines 46, that read stored charges from storage capacitors 36 via those TFTs 38 which have been turned ON, are arranged in the direction of arrow B (which is perpendicular to the direction of arrow A).

Signal detection correction section 22 is provided with a gate line driver 48 connected to each individual gate line 44 of radiation ray detection panel 14. Gate line driver 48, upon reading signal charges from radiation ray detection panel 14, performs a gate line control process with respect to each gate wiring 44 in turn, where, by supplying a high level voltage signal (an ON signal) to a particular gate wiring 44, it changes from OFF to ON a TFT 38 of a pixel portion 40 connected to the particular gate wiring 44 which has been sent the ON signal, and after a certain period of time, by ceasing supply of the ON signal to the particular gate wiring 44, changes from ON to OFF said TFT 38 of the pixel portion 40 which is connected to the particular gate wiring 44 to which the ON signal was supplied.

Signal detection correction section 22 is provided with a number of operational amplifiers 50 equal to the number of data lines 46 provided to TFT active matrix substrate 34. Each data line 46 of radiation ray detection panel 14 is connected to a different operational amplifier 50, at an inverting input terminal thereof. Each operational amplifier 50 is connected to GND (ground) wiring at respective non-inverting input terminals thereof, and to one ends of respective capacitors 52 at inverting input terminals thereof, the other ends of respective capacitors 52 being connected to output terminals thereof. As a result of the above configuration, respective operational amplifiers 50 and capacitors 52 perform integration with respect to the currents (signal charges) of data lines 46 connected to said inverting input terminals, and function as charge amplifiers that output a signal having a level corresponding to the result of the integration.

The output terminals of respective operational amplifiers 50 (charge amplifiers), are connected to respective plural input terminals of a multiplexer 54 via an amplifier or a sample holding circuit (both not shown), and output signals of each charge amplifier are input in parallel to multiplexer 54. An output terminal of multiplexer 54 is connected to an input terminal of an A/D (analog to digital) converter 56. Multiplexer 54 selects each of the plural input terminals in turn, and outputs a signal input from the selected input terminal to A/D converter 56. Thereby, each of plural signals (the same number as the number of data lines 46) input in parallel to multiplexer 54, are converted from parallel to serial and from analog to digital signals.

An output terminal from A/D converter 56 is connected to an input terminal of image quality correction processing section 58. An output terminal of image quality correction processing section 58 is connected to control section 24 (see FIG. 1). Image quality correction processing section 58 performs leak correction processing and electrical noise suppression processing as image quality correction processing in order to increase image quality, and subsequently outputs image quality correction processed data (image data) to control section 24.

In order to protect TFTs 38 when irradiating with a large dose of radiation rays, radiation ray detection panel 14 of the present embodiment adopts a configuration whereby charges due to the irradiation of radiation rays stored in storage capacitors 36 of individual pixel portions 40 are actively made to flow through data lines 46 as leak current. As a result, during a period in which gate line driver 48 is not supplying an ON signal to any gate wiring 44, only a leak current flows through data line 46, and during a period in which gate line driver 48 is sending an ON signal to any gate wiring 44, a current corresponding to a signal charge stored in a storage capacitor 36 is superposed with a leak current and the resulting current flows through data line 46. Further, leak current flowing through data line 46 weakens over time and becomes 0. If the result of current flowing at data line 46 is integrated by a charge amplifier and used without modification as image information, a band-shaped image defect (artifact), extending in a vertical direction from a high dosage emission area of the image, is generated (the developed artifact is known as a "trail").

For this reason, image quality correction processing section 58 performs leak correction to correct the effect of leak current, by performing, with respect to the charge amplifier, and for each individual gate wiring 44, integration of the current (signal charge) flowing through data lines 46 for each of an ON period when TFT 38 is on, and an OFF period when TFT 38 is not on, and then subtracting the data of the OFF period from the data of the ON period. Further, since negative effects occur in processing in which the OFF period data is simply subtracted from the ON data, including electrical noise increasing by $\sqrt{2}$ times, and generation of image deficiencies (artifacts) where white areas occur in an image, a moving average of the OFF period data (for example, a moving average with a range of several pixels in a main scanning direction (a direction of gate wiring 44) and a sub-scanning direction (a direction of data line 46)) may be calculated, and this moving average data of the OFF period may be subtracted from the data of the ON period.

Image quality correction processing section 58 performs electrical noise suppression, in which the same analog signal is input to A/D converter 56 plural times, A/D conversion is performed on the same analog signal plural times, and an average value of the digital data obtained from the A/D conversion is output as image data. As a result of the electrical noise processing, random noise added to digital data at the time of A/D conversion by A/D converter 56 is suppressed.

However, when leak correction processing is performed by image quality correction processing section 58, a required time from the start of reading of an image from radiation ray detection panel 14 to the output of image data to control section 24 (reading and correction time) doubles in comparison to when leak correction processing is not performed, and when image quality correction processing section 58 performs electrical noise suppression of A/D conversion four times, the reading and correction time is four times longer than when suppression of electrical noise is not performed. As a result, image quality correction processing section 58 according to the present embodiment may be switched between performing or not performing each of leak correction processing or electrical noise suppression processing, and only performs leak correction processing or electrical noise suppression processing if instructed to by control section 24. Signal detection correction section 22, which includes image quality correction processing section 58 corresponds to a correction unit of the present invention.

Next, the operation of the present embodiment will be explained. In the present embodiment, information such as an imaging time interval between multiple imagings (for example, two) for forming an energy subtraction image, a tube voltage of radiation ray generation section 12 for each imaging, whether image quality correction processing is performed at each imaging, and which each image is to be output as an image for use in diagnosis, are stored in advance in an imaging conditions information database stored in storage section 24A of control section 24, for each imaging region of subject 18 which can be imaged by radiation imaging system 10, as exemplified in Table 1.

TABLE 1

Example of Imaging Conditions Information

| | First Imaging | | | Second Imaging | | |
|---|---|---|---|---|---|---|
| Imaging region | Tube Voltage | Image Quality Correction Processing | Imaging Time interval | Tube Voltage | Image Quality Correction Processing | Image for Diagnosis |
| Chest | 60 kV | No | 200 ms | 120 kV | Yes | Second Image |
| Lumbar Spine | 80 kV | Yes | 500 ms | 120 kV | No | First Image |
| Limb | 50 kV | Yes | 500 ms | 120 kV | No | First Image |
| Breast | 25 kV | Yes | 500 ms | 50 kV | No | First Image |

In Table 1, "First Image" and "Second Image" indicated in the column "Image for Diagnosis" means that the first image or the second image obtained from the first imaging or the second imaging, respectively, is output as an image for use in diagnosis. Storage section 24A corresponds to the storage section of the present invention.

Figure 3A:
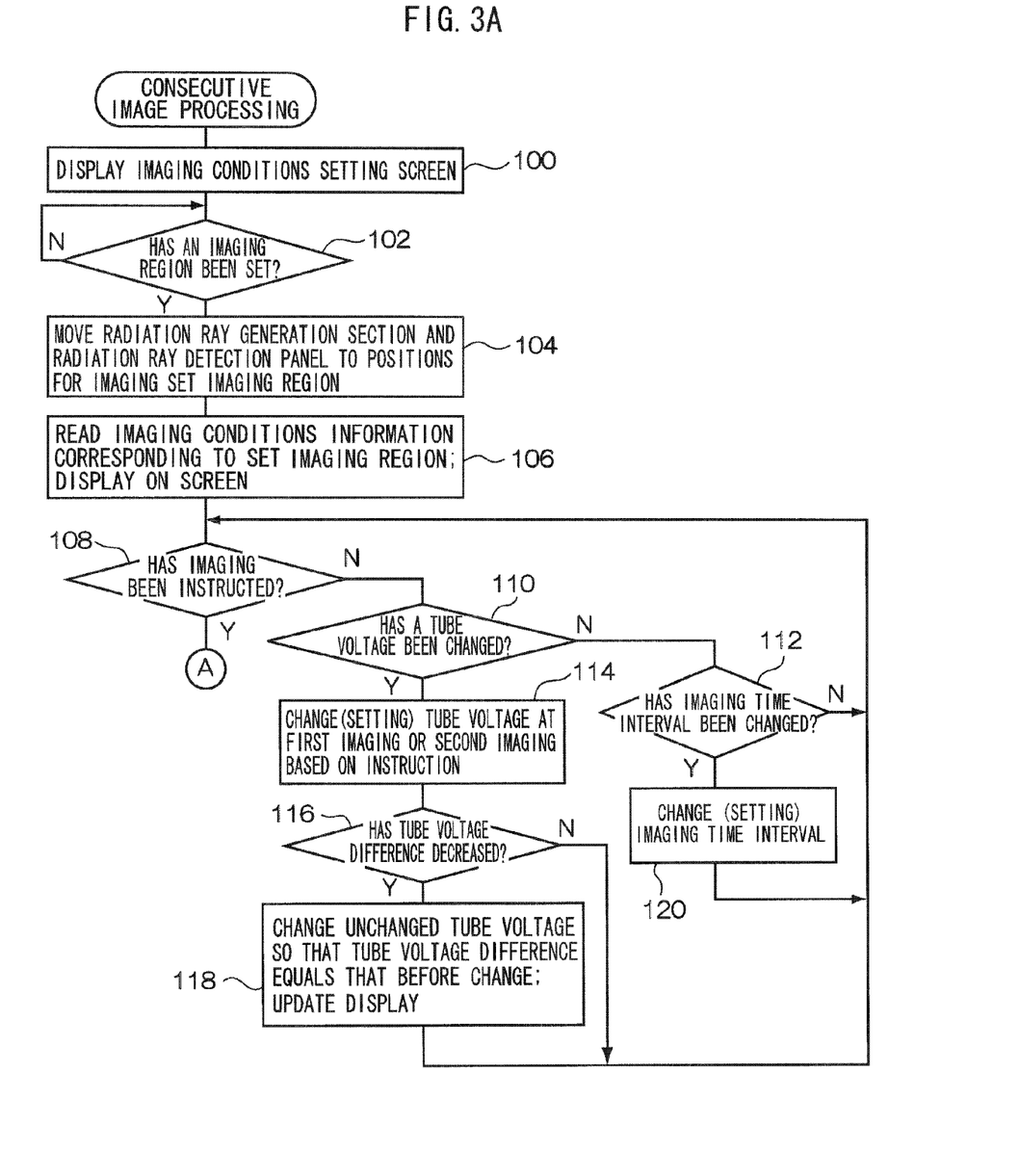
FIGS. 3A and 3B are flowcharts showing the content of a consecutive imaging process performed by a control section.
Figure 3B:
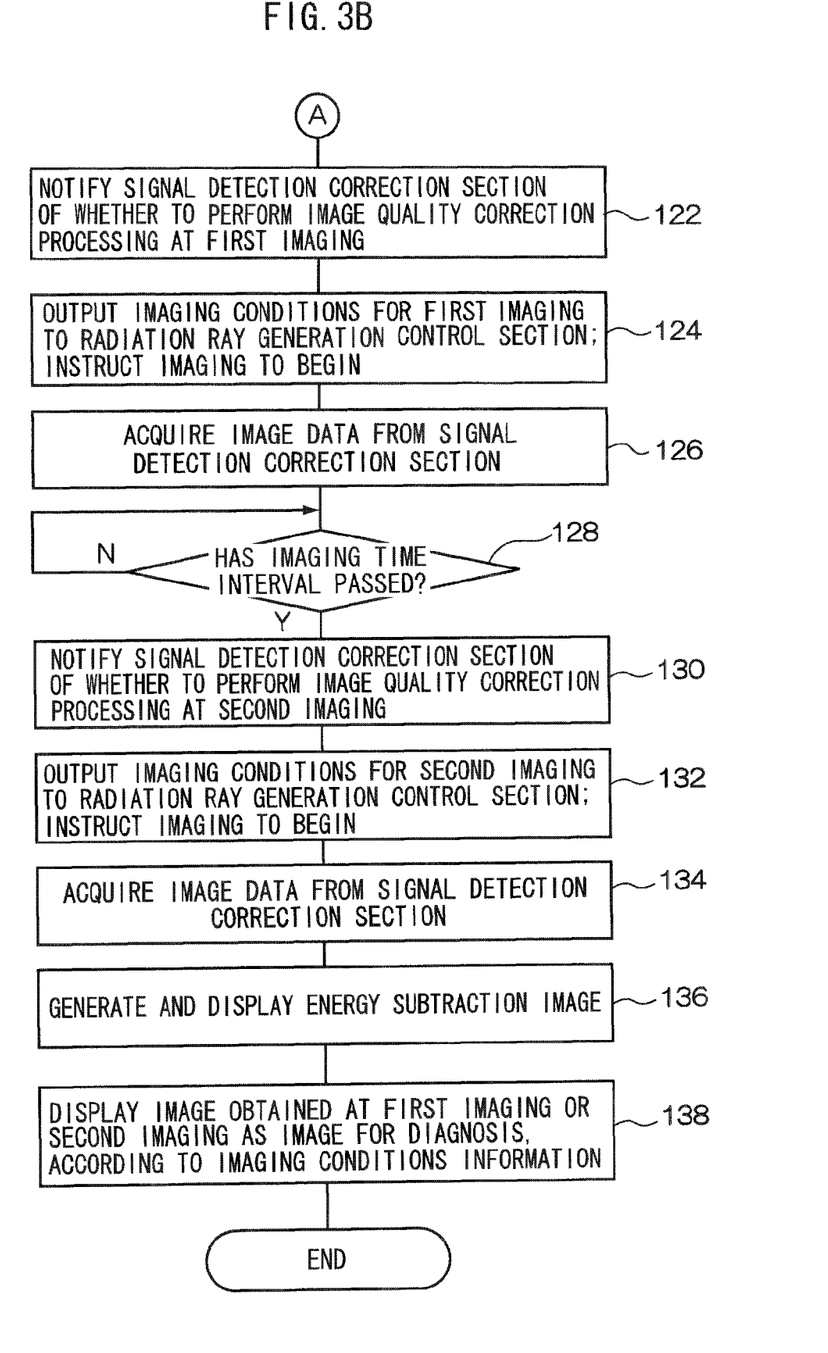

Next, a consecutive imaging processing performed by control section 24, when a user operates operation panel 28 and instructs the performing of plural imagings to create an energy subtraction image, will be explained with reference to FIGS. 3A and 3B.

Figure 4:
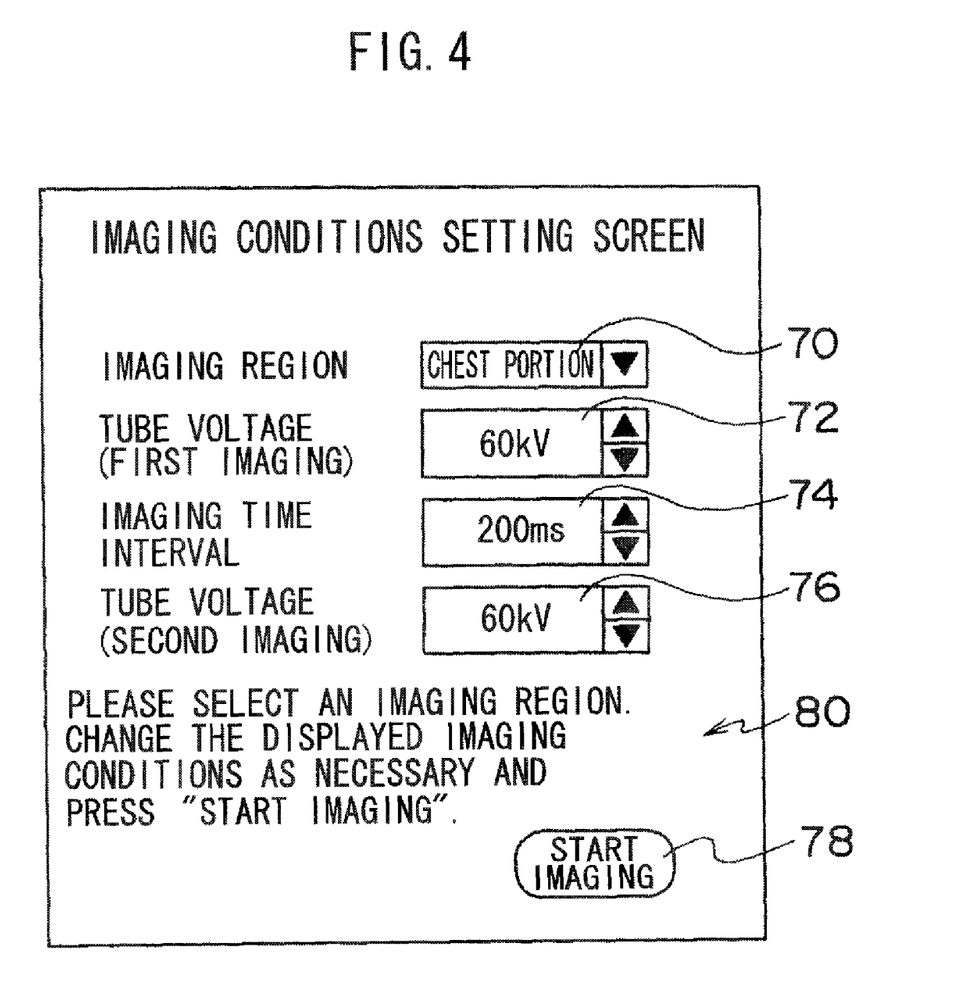
FIG. 4 is a concept drawing showing an example of an imaging conditions setting screen.

In the consecutive imaging processing, in first step 100, an imaging conditions setting screen is displayed at display 26 such as that as shown in FIG. 4. As shown in FIG. 4, the imaging conditions setting screen according to the present embodiment includes a setting/display field 70, for setting and displaying an imaging region, a setting/display field 72 for setting (in order to change) and displaying a tube voltage of radiation ray generation section 12 at the first imaging, a setting/display field 74 for setting (in order to change) and displaying an imaging time interval, a setting/display field 76 for setting (in order to change) and displaying a tube voltage of radiation ray generation section 12 at the second imaging, a button 78 to instruct imaging to begin, and a message 80 that requests the user to select an imaging region, to change imaging conditions if necessary, and to instruct imaging to begin. Further, when the imaging conditions setting screen is first displayed at display 26, setting/display fields 70-78 are each blank.

In the next step 102, it is determined whether or not the user has selected an imaging region, and step 102 repeats until the determination thereof is affirmative. The user reviews the imaging conditions setting screen displayed at display 26, and by referring to message 80 displayed within this screen, realizes that it is necessary to set an imaging region, and by operating operation panel 28, the user sets setting/display field 70 to the imaging region which is to be imaged. When this operation is performed by the user, the determination of step 102 is affirmative and processing moves to step 104, where the imaging region selected by the user in setting/display field 70 is recognized, and imaging region movement section 30 moves radiation ray generation section 12 and radiation ray detection panel 14 to respective positions at which the recognized imaging region can be imaged.

In step 106, imaging conditions information corresponding to the imaging region recognized in step 104 (the imaging region selected by the user) is read to a memory from an imaging conditions information database, and from among the read imaging conditions information, the tube voltage of radiation ray generation section 12 at the first imaging is displayed at setting/display field 72 within the screen, an imaging time interval is displayed at setting/display field 74 within the screen, and the tube voltage of radiation ray generation section 12 at the second imaging is displayed at setting/display field 76 within the screen. Thereby, by reviewing the displayed imaging conditions information setting screen, the user can be aware of the current imaging conditions (the tube voltage of radiation ray generation section 12 at each of the first and second imagings, and the imaging time interval).

In step 108, it is determined whether or not the user has instructed imaging to begin. If this determination is negative, then processing moves to step 110, and it is determined whether or not the user has instructed the tube voltages to be changed for the first or the second imaging. If this determination is negative, processing moves to step 112, and it is determined whether or not the user has instructed the imaging time interval to be changed. If this determination is negative, processing returns to step 108. Steps 108 to 112 are repeated until any of the above determinations is positive.

If the user, who is aware of the current imaging conditions by referring to the displayed imaging conditions setting screen, judges that, based on the bodily frame of subject 18 (a subject of imaging), it is necessary to change the tube voltage of radiation ray generation section 12, the user operates operation panel 28, and changes the tube voltage of radiation ray generation section 12 at the first imaging, which is shown at setting/display field 72, or the tube voltage of radiation ray generation section 12 at the second imaging, which is shown at setting/display field 76. If the user has performed an operation such as the above, it is determined that the tube voltage has been instructed to be changed by the user, and since the determination at step 110 is affirmative, processing moves to step 114, where from among the imaging conditions information read from an imaging conditions information database and retained in a memory, the tube voltage instructed to be changed by the user for the first or second imaging is set to be changed.

In the next step 116, concomitant with the set (change) to the tube voltage in step 114, it is determined whether the difference in tube voltages between the tube voltage at the first imaging and at the second imaging has decreased. As shown in Table 1, in the present embodiment, regardless of the imaging region, the tube voltage at the first imaging is to be less than that at the second imaging (the tube voltage is set such that the dose of radiation rays increases monotonically between each imaging). Therefore, determination at step 116 is affirmative if the tube voltage at the first imaging has been increased by the user, or if the tube voltage at the second imaging has been decreased by the user.

If the determination at step 116 is affirmative, then the change to the tube voltage by the user has resulted in a decrease in the difference between the tube voltage at the first imaging and the tube voltage at the second imaging, which may result in a decrease in image quality of an energy subtraction image, such as a decrease in contrast. Therefore, processing moves to step 118, and the one of the tube voltage at the first imaging or the tube voltage at the second imaging which was not changed at step 114 is changed such that the difference between the tube voltage at the first imaging and the tube voltage at the second imaging becomes equal to the difference in tube voltages indicated by the imaging conditions information stored in the imaging conditions information database (for example, if the user increases the tube voltage at the first imaging, the tube voltage at the second imaging is increased by the same amount, and if the user decreases the tube voltage at the second imaging, the tube voltage at the first imaging is decreased by the same amount), and processing then returns to step 108.

As a result, it is possible to prevent a decrease in image quality of an energy subtraction image, such as a decrease in contrast resulting from a change to the tube voltage by the user. Further, when the user changes one of the tube voltage at the first imaging or the tube voltage at the second imaging, and the difference between the tube voltages decreases, the other tube voltage is automatically changed, and therefore there is no need for the user to consider a decrease in contrast of the energy subtraction image when changing tube voltages, and as a result changing the tube voltage can be easily performed by a user.

If the determination at step 116 is negative (the tube voltage at the first imaging is decreased by the user, or the tube voltage at the second imaging is increased by the user), the change of the tube voltage by the user results in an increase in the difference between the tube voltage at the first imaging and the tube voltage at the second imaging, and it is possible to infer from this that a decrease in contrast of the energy subtraction image will not occur, and therefore, processing returns to step 108 without performing any further processing. However, instead of this, similar to as in step 118, the one of the tube voltage at the first imaging or the tube voltage at the second imaging which was not changed at step 114 may be changed such that the difference between the tube voltage at the first imaging and the tube voltage at the second imaging becomes equal to the difference indicated by the imaging conditions information stored in the imaging conditions information database (for example, if the tube voltage at the first imaging is decreased by the user, the tube voltage at the second imaging may be decreased by the same amount, and if the tube voltage at the second imaging is increased by the user, the tube voltage at the first imaging may be increased by the same amount).

If the user, who is aware of the current imaging conditions by referring to the displayed imaging conditions setting screen, judges that it is necessary to change the imaging time interval, the user operates operation panel 28 and changes the imaging time interval displayed in setting/display field 74. When the user performs the above operation, it is determined that an instruction to change the imaging time interval has been issued by the user, and the determination of step 112 is affirmative. Processing subsequently moves to step 120, and from among imaging conditions information read from an imaging conditions information database and retained in a memory, an imaging time interval is set to be changed and processing returns to step 108.

In this manner, in the present embodiment, an imaging time interval can be set to be changed by a user, and thereby, if for example, a chest portion of subject 18 (an imaged person) is to be imaged, then the cardiac cycle of the imaged person may be measured, and the user can change the imaging time interval to approach the measured cardiac cycle, and thereby reduce motion artifacts in an energy subtraction image.

By performing operations as described above that instruct imaging conditions (tube voltage and imaging time interval) to be changed as necessary, a user, who has confirmed whether or not imaging conditions displayed at an imaging conditions setting screen are appropriate, operates operation panel 28 and selects button 78 within the screen. When button 78 is selected, it is judged that the user has instructed imaging to begin, and since the determination of step 108 is affirmative, processing moves to step 122. At step 122, from among the current imaging conditions information retained in a memory, information regarding whether image quality correction processing is to be performed at the first imaging is referenced, and based on this information, image quality correction processing section 58 is instructed to perform, or not perform, image quality correction processing. In the next step 124, imaging conditions for the first imaging (a tube voltage) set in the current imaging conditions information retained in a memory are sent to radiation ray generation control section 20, and an instruction is to perform imaging is given.

Radiation ray generation control section 20 controls the tube voltage when radiation ray generation section 12 is to generate radiation rays such that it matches the tube voltage sent from control section 24 while radiation rays are generated at radiation ray generation section 12. The radiation rays generated at radiation ray generation section 12 are irradiated at an imaging region, set by the user, of subject 18 positioned at an imaging position, pass through the imaging region, are incident at radiation ray detection panel 14, and are stored as charges at storage capacitor 36 of pixel portion 40 of radiation ray detection panel 14. When generation of radiation rays by radiation ray generation section 12 is complete, reading of image information (signal charges) from (storage capacitor 36 of pixel portion 40 of) radiation ray detection panel 14 by signal detection correction section 22 is performed. In previous step 122, when image quality correction processing section 58 is instructed to perform image quality correction processing, image quality correction processing is performed by image quality correction processing section 58 in parallel with reading of image information from radiation ray detection panel 14.

In the next step 126, image data is acquired from signal detection correction section 22, and the acquired image data is stored at storage section 24A or the like as image data obtained at the first imaging. In step 128, radiation ray generation section 12 generates radiation rays in the first imaging, and it is determined whether or not a period of time corresponding to the imaging time interval, set in the current imaging conditions information stored in a memory, has passed, and step 128 is repeated until the result of this determination is affirmative. When the determination of step 128 is affirmative, processing moves to step 130, and from the current imaging conditions information stored in memory, information indicating whether image quality correction processing is to be performed at the second imaging is referenced, and, based on this information, image quality correction processing section 58 is instructed to perform, or not perform, image quality correction processing. In step 132, imaging conditions (tube voltage) in the second imaging which are set to the current imaging conditions information stored in memory, are sent to radiation ray generation control section 20, and an instruction to perform imaging is given.

Thus, radiation ray generation control section 20 controls the tube voltage when radiation ray generation section 12 is to generate radiation rays, such that it matches the tube voltage sent from control section 24, and radiation rays are generated at radiation ray generation section 12. The radiation rays generated at radiation ray generation section 12 are irradiated at the same imaging region as in the first imaging of subject 18 positioned at the imaging position, pass through the imaging region, are incident at radiation ray detection panel 14, and are stored as charges at storage capacitors 36 of pixel portions 40 of radiation ray detection panel 14. When generation of radiation rays by radiation ray generation section 12 is complete, reading of image information (signal charges) from (storage capacitor 36 of pixel portion 40 of) radiation ray detection panel 14 by signal detection correction section 22 is performed. In step 130, when image quality correction processing section 58 is instructed to perform image quality correction processing, image quality correction processing is performed by image quality correction processing section 58 in parallel with reading of image information from radiation ray detection panel 14.

In the next step 134, image data is acquired from signal detection correction section 22, and the acquired image data is stored at storage section 24A or the like as image data obtained at the second imaging. In step 136, image data respectively obtained at the first and second imagings and stored in storage section 24A are assigned different predetermined weights and a differential is calculated, thereby generating an energy subtraction image which is displayed at display 26. In step 138, based on information of the current imaging conditions information stored in the memory determining an image for diagnosis, the image obtained at the first imaging and/or the image obtained at the second imaging is judged to be an appropriate image for diagnosis, and displayed as an image used for diagnosis at display 26, and processing ends. At steps 136 and 138, a user may instruct images to be displayed at display 26.

Further, the imaging conditions setting screen and flow of processing is not limited to the above, and an imaging region may be determined in advance, with only the tube voltage and imaging time interval being settable.

Amongst the imaging regions indicated in Table 1, since in a chest portion a heart that moves due to an involuntary muscle is within the imaging range, an imaging time interval has a large influence on the generation of motion artifacts. Moreover, in radiation ray imaging of a chest portion, from among plural images obtained from plural imagings at different radiation ray doses and tube voltages, an image taken with radiation rays under a high tube voltage is most appropriate as an image for diagnosis. Based on the above, the present embodiment, as shown in Table 1, with respect to a chest region, designates the image obtained at the second imaging as an image for diagnosis, and does not use the image obtained at the first imaging for diagnosis or the like. Therefore, image quality correction processing at the first imaging is set to "No". Since a radiation ray dose at the first imaging is set comparatively low, and image quality correction processing at the first imaging is set to "No", as shown in Table 1, the imaging time interval when imaging a chest region is much shorter than when imaging other regions. As a result, motion artifacts of an energy subtraction image can be reduced. Moreover, since image quality correction processing at the second imaging is set to "Yes", a high quality image for diagnosis can be obtained.

Since, in the imaging regions shown in Table 1 other than a chest portion (lumbar spine, a limb, a breast and so on), organs that move due to an involuntary muscle do not enter the imaging range, an imaging time interval does not have a large influence on the creation of motion artifacts. Moreover, in radiation ray imaging of these regions, from among plural images obtained from plural imagings at different radiation ray doses and tube voltages, an image taken with radiation rays under a lower tube voltage is most appropriate for an image for diagnosis. Based on the above, the present embodiment, as shown in Table 1, with respect to regions other than a chest region, designates the image obtained at the first imaging an image for diagnosis, and image quality correction processing at the first imaging is set to "Yes". Since the radiation ray dose at the first imaging is comparatively large, and image quality correction processing at the first imaging is set to "Yes", as shown in Table 1, an imaging time interval is much larger than that for the chest portion. As a result, a high quality image for diagnosis can be obtained. Further, since an imaging time interval does not greatly influence the generation of motion artifacts in imaging regions other than a chest portion, motion artifacts in an energy subtraction image can be reduced by externally holding the imaging region, or other means such as requesting the imaged subject not to move the imaging region.

The above explains an aspect of the present invention applied to the creation of an energy subtraction image. However, the present invention is not limited thereto, and the present invention may, for example, also be applied in the creation of frame-by-frame animation (semi-animation), by setting a constant radiation ray dose and tube voltage.

There is a demand for diagnosis in which movement in a series of animated images is analyzed. In the analysis of this movement, the required time between images differs depending on the imaging region. As an example of use thereof, the movement of the lungs at a chest portion during breathing may be observed via animated images and diagnosis performed accordingly. Since there is a high demand for viewing detailed movement of the lungs by images taken with only a short space of time therebetween, an imaging time interval can be reduced accordingly. Further, as another use, by using animations of the lumbar spine or the bones of the limbs, it can be determined whether joints and bones are moving correctly. These movements do not require a particularly large time interval between images, and can be controlled easily by a patient compared to breathing, and therefore an imaging time interval may be large. Further, it is easy to reduce imaging time for imaging of a chest portion with a high tube voltage. Thus, by making an imaging time interval short for a chest portion and long for a lumbar spine or the limbs, images suitable for each region can be provided.

The above includes, as an example of the image detection unit according to the present invention, an explanation of radiation ray detection panel 14 which is provided with a charge conversion layer that directly converts irradiated radiation rays to charges. However, the present invention is not limited thereto, and the photoelectric conversion portion of the image detection unit that converts irradiated radiation rays to charges may have a configuration in which it converts irradiated radiation rays to electromagnetic waves (visible light or the like) and subsequently converts the electromagnetic waves to charges (indirect conversion). Further, the above includes explanation of a structure in which a photoelectric conversion layer is formed on TFT active matrix substrate 34; however, the above photoelectric conversion portion may be provided separately from a substrate in which plural pixel portions each having a storage capacitor and a switching portion are arranged.

The above includes explanation of an example of radiation ray detection panel 14 having a configuration in which plural pixel portions 40 (TFTs 38 and storage capacitors 36) are arranged in a matrix (2-dimensionally). However, the present invention is not limited thereto, and the radiation ray detection panel may have a configuration in which plural pixel portions are arranged in a line (1-dimensionally).

The above also includes disclosure relating to X-rays as an example of radiation rays generated by the radiation ray generation unit according to the present invention. However, the present invention is not limited thereto, and other radiation rays may be used, such as electron rays or α rays, provided that they are converted to electrical charges at the image detection unit and the charges are stored in storage capacitors.

What is claimed is:

1. A radiation imaging device, comprising:
a radiation ray generation unit that generates radiation rays;
an image detection unit that detects as an image radiation rays that are emitted by the radiation ray generation unit and pass through a subject;
a subtraction image forming unit that forms a subtraction image by using detected images; and
a control unit that, when the same subject is to be imaged consecutively plural times, changes an imaging time interval between imagings according to a set imaging region of the subject; wherein
when the same subject is to be imaged consecutively plural times, the control unit controls the radiation ray generation unit so that a radiation ray tube voltage at each imaging increases monotonically, regardless of the set imaging region of the subject; and wherein
the control unit determines which is output between an image obtained at a first imaging or an image obtained at a second imaging, according to the set imaging region of the subject.

2. The radiation imaging device of claim 1, wherein when the same subject is to be imaged consecutively plural times, the control unit controls the radiation ray generation unit so that a radiation ray dose at each imaging increases monotonically, regardless of the set imaging region of the subject.

3. The radiation imaging device of claim 1, further comprising a storage section that stores set values of an imaging time interval between plural imagings with respect to each imaging region of a subject; wherein the control unit reads the set value of the imaging time interval from the storage section according to the set imaging region of the subject, and uses the value for control of the imaging time interval.

4. The radiation imaging device of claim 3, further comprising an instruction section, wherein the control unit, when instructed to change an imaging time interval via the instruction section, changes a value of the imaging time interval read from the storage section in accordance with the instruction, and uses the changed value for control of the imaging time interval.

5. The radiation imaging device of claim 3, wherein parameters that determine imaging conditions for each imaging of plural imagings are stored with respect to each imaging region in the storage section; and the control unit reads the parameters corresponding to the set imaging region of a subject from the storage section, and uses the parameters for control of imaging conditions for each imaging of plural imagings.

6. The radiation imaging device of claim 5, wherein, when imaging conditions for a particular instance of imaging of plural imagings are changed via the instruction section, the control unit changes the imaging conditions for the particular instance of imaging of plural imagings set by parameters read from the storage section, and changes imaging conditions for a different instance of imaging of the plural imagings based on the changed imaging conditions of the particular instance of imaging.

7. The radiation imaging device of claim 6, wherein the imaging conditions include a tube voltage of the radiation ray generation unit; and when the tube voltage is changed in the particular instance of imaging, the control unit changes the tube voltage for an instance of imaging different from the particular instance of imaging, such that a difference in tube voltages between plural imagings is not less than a difference in tube voltage determined by a parameter read from the storage section.

8. The radiation imaging device of claim 1, further comprising a correction unit that, between respective imagings, while acquiring from the image detection unit an image detected by the image detection unit, performs image quality correction processing to improve image quality of the acquired image, wherein the control unit switches between the correction unit performing and not performing image quality correction processing according to the set imaging region of the subject.

9. The radiation imaging device of claim 8, wherein the image detection unit is provided with plural pixel portions each provided with a switching portion that switches ON and OFF according to an ON or OFF signal supplied via a first signal line, and a retaining portion that retains a signal charge corresponding to an irradiated radiation ray dose, and the correction unit, as image quality correction processing, respectively acquires a signal output from a second signal line at each of when the switching portion is ON or OFF, and performs at least one of a leak correction processing, in which an OFF output signal is subtracted from an ON input signal, or an electronic noise suppression processing, in which an output signal is converted to digital data plural times and averaged.

10. The radiation imaging device of claim 1, further comprising a correction unit that, between respective imagings, while acquiring from the image detection unit an image detected by the image detection unit, performs image quality correction processing to improve image quality of the acquired image, wherein the control unit switches between the correction unit performing and not performing image quality correction processing for each imaging as a unit with respect to plural imagings.

11. A radiation imaging method, comprising:
generating radiation rays consecutively plural times with respect to a single subject;
performing plural imagings by detecting as images radiation rays that pass through the subject;
controlling to change an imaging time interval between the respective plural imagings according to a set imaging region of the subject; and
increasing a radiation ray dose at each imaging monotonically, regardless of the set imaging region of the subject.

12. The radiation imaging method of claim 11, further comprising increasing a radiation ray tube voltage at each imaging monotonically, regardless of the set imaging region of the subject.

13. The radiation imaging method of claim 11, further comprising according to the set imaging region of the subject, determining which between an image obtained at a first imaging or an image obtained at a second imaging is output in a radiation imaging device as an image for diagnosis.

14. The radiation imaging method of claim 11, further comprising: storing a set value for an imaging time interval between plural imagings in advance in a storage section for each imaging region of a subject, and controlling the imaging time interval by using the set value.

15. The radiation imaging method of claim 14, further comprising: based on an instruction that an imaging time interval is to be changed, changing the set value according to the instruction, and controlling the imaging time interval using the changed set value.

16. The radiation imaging method of claim 14, further comprising: storing parameters that determine imaging conditions for each imaging of plural imagings with respect to each imaging region of a subject in the storage section, and controlling the imaging conditions for each imaging of plural imagings using the parameters stored in the storage section.

* * * * *